United States Patent [19]

Hoffmann et al.

[11] 3,985,874

[45] Oct. 12, 1976

[54] O-[1-ALKYL- OR-PHENYL-5-ALKYLMERCAPTOALKYL-MERCAPTO-1,2,4-TRIAZOL(3)YL]-(THIONO)-PHOSPHORIC(PHOSPHONIC, PHOSPHINIC) ACID ESTERS AND ESTER-AMIDES

[75] Inventors: Hellmut Hoffmann, Wuppertal; Ingeborg Hammann, Cologne; Bernhard Homeyer, Opladen, all of Germany

[73] Assignee: Bayer Aktiengesellschaft, Leverkusen, Germany

[22] Filed: Apr. 29, 1975

[21] Appl. No.: 573,273

[30] Foreign Application Priority Data
May 9, 1974    Germany.......................... 2422548

[52] U.S. Cl............................. 424/200; 260/308 R; 260/308 C; 260/959; 260/960
[51] Int. Cl.²........................ A01N 9/36; C07 9/65
[58] Field of Search................. 260/308 R; 424/200

[56] References Cited
UNITED STATES PATENTS

| | | | |
|---|---|---|---|
| 2,754,244 | 7/1956 | Gysin et al. | 260/310 R |
| 3,867,398 | 2/1975 | Bohner et al. | 260/308 R |

FOREIGN PATENTS OR APPLICATIONS

| | | | |
|---|---|---|---|
| 2,259,960 | 6/1973 | Germany | 260/308 R |

*Primary Examiner*—Alton D. Rollins
*Attorney, Agent, or Firm*—Burgess, Dinklage & Sprung

[57] ABSTRACT

O-[1-alkyl- or-phenyl-5-alkylmercaptoalkyl-mercapto-1,2,4-triazol(3)yl]-(thiono)-phosphoric(phosphonic, phosphinic) acid esters and ester-amides of the formula

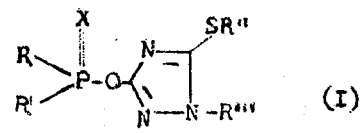

in which
  R is alkyl or alkoxy, each with 1 to 6 carbon atoms,
  R' is alkyl, alkoxy or alkylamino, each with 1 to 6 carbon atoms, or phenyl,
  R'' is alkylmercaptoalkyl with 1 to 4 carbon atoms in each alkyl moiety,
  R''' is alkyl with 1 to 4 carbon atoms or phenyl, and
  X is oxygen or sulfur,
which possess insecticidal, acaricidal and nematocidal properties.

10 Claims, No Drawings

O-[1-ALKYL- OR-PHENYL-5-ALKYLMERCAPTOALKYL-MERCAPTO-1,2,4-TRIAZOL(3)YL]-(THIONO)-PHOSPHORIC(PHOSPHONIC, PHOSPHINIC) ACID ESTERS AND ESTER-AMIDES

The present invention relates to and has for its objects the provision of particular new O-[1-alkyl-or -phenyl-5-alkylmercaptoalkylmercapto-1,2,4-triazol(-3)yl-(thiono)-phosphoric(phosphonic, phosphinic) acid esters and ester-amides which possess insecticidal, acaricidal and nematocidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It is known from U.S. Pat. No. 2,754,244 and German Published Specification DOS 2,259,960 that pyrazolothionophosphoric acid esters, for example O,O-diethyl-(Compound A) and O,O-dimethyl-O-[3-methyl-pyrazol(5)yl]-thionophosphoric acid esters (Compound B) and triazolothiono-phosphoric acid esters, for example O,O-dimethyl-(Compound C) and O,O-diethyl-O-[1-methyl-5-methylmercapto-1,2,4-triazol(3)yl]- (Compound D) and O,O-dimethyl-O-[1-ethyl-5-methylmercapto-1,2,4-triazol(3)yl]- (Compound E) and O,O-dimethyl-O-[1-isopropyl-5-methylmercapto-1,2,4-triazol(3)yl]-thionophosphoric acid esters (Compound F), possess insecticidal and acaricidal properties.

The present invention provides O-triazolyl-(thiono)-phosphoric(phosphonic, phosphinic) acid esters and ester-amides of the general formula

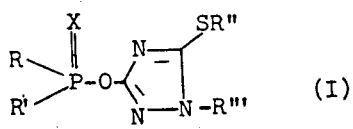

in which
R is alkyl or alkoxy, each with 1 to 6 carbon atoms,
R' is alkyl, alkoxy or alkylamino, each with 1 to 6 carbon atoms, or phenyl,
R'' is alkylmercaptoalkyl with 1 to 4 carbon atoms in each alkyl moiety,
R''' is alkyl with 1 to 4 carbon atoms or phenyl, and
X is oxygen or sulfur.

Preferably, R is straight-chain or branched alkyl or alkoxy with 1 to 4, especially 1 to 3, carbon atoms; R' is straight-chain or branched alkyl, alkoxy or monoalkylamino with 1 to 5, especially 1 to 3, carbon atoms, or phenyl; R'' is alkylmercaptoalkyl with 1 to 3, especially 1 or 2, carbon atoms in each alkyl moiety; and R''' is alkyl with 1 to 3, especially 1 or 2, carbon atoms, or phenyl.

Surprisingly, the O-triazolyl-(thiono)-phosphoric(phosphonic, phosphinic) acid esters and ester-amides according to the invention have a better insecticidal, including soil-insecticidal, acaricidal and nematocidal action than the previously known compounds of analogous structure and of the same type of action. Furthermore they are active not only against insects and mites which damage plants, but also against hygiene pests and pests of stored products. The compounds according to the invention thus represent a genuine enrichment of the art.

The invention also provides a process for the production of an O-triazolyl-(thiono)-phosphoric(phosphonic, phosphinic) acid ester or ester-amide of the formula (I) in which a (thiono)-phosphoric(phosphonic, phosphinic) acid diester halide or ester halide or ester-amide halide of the general formula

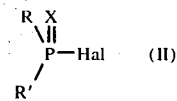

in which
R, R' and X have the abovementioned meanings, and Hal is halogen, preferably chlorine,
is reacted with a 1-alkyl- or 1-phenyl-3-hydroxy-5-alkylmercaptoalkyl-mercapto-triazole derivative of the general formula

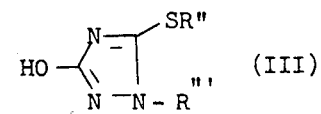

in which
R'' and R''' have the abovementioned meanings, in the presence of an acid acceptor or in the form of an alkali metal salt, alkaline earth metal salt or ammonium salt.

If, for example, O,O-dimethylthionophosphoric acid diester chloride and 1-phenyl-3-hydroxy-5-methylmercaptomethylmercaptotriazole-(1,2,4) are used as starting materials, the course of the reaction can be represented by the following formula scheme:

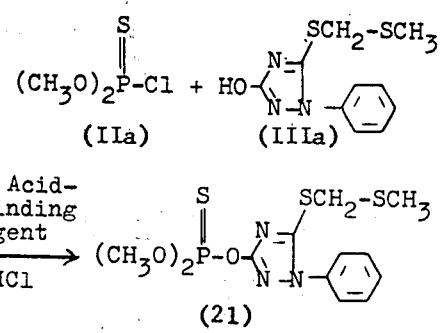

The (thiono)phosphoric(phosphonic, phosphinic) acid ester halides and ester-aimide halides (II) are known from the literature and can be prepared according to customary methods, even on a large industrial scale.

The following may be mentioned as individual examples of the above starting materials: O,O-dimethyl-, O,O-diethyl-, O,O-di-n-propyl, O,O-di-iso-propyl-, O,O-di-n-butyl-, O,O-di-iso-butyl-, O,O-di-tert.-butyl, O-ethyl-O-n-propyl-, O-ethyl-O-iso-propyl- and O- ethyl-O-sec.-butyl-phosphoric acid ester, and also O-methyl-, O-ethyl-, O-n-propyl-, O-iso-propyl-, O-n-butyl-, O-sec.-butyl-, O-iso-butyl- or O-tert.-butyl-methane-, -ethane, -n-propane-, -iso-propane-, -n-butane-, -iso-butane-, -sec.-butane-, -tert.-butane- or benzene-phosphonic acid ester chloride, O-methyl-N-methyl-, O-methyl-N-ethyl-, O-methyl-N-n-propyl-, O-methyl-N-iso-propyl-, O-methyl-N-n-butyl-, O-methyl-N-iso-butyl-, O-methyl-N-tert.-butyl-, O-methyl-N-sec.-butyl-, O-ethyl-N-methyl-, O-ethyl-N-ethyl-, O-ethyl-N-n-propyl-, O-ethyl-N-iso-propyl-, O-ethyl-N-n-butyl-, O-ethyl-N-iso-butyl-, O-ethyl-N-sec.-butyl-, O-ethyl-N-tert.-butyl-, O-n-propyl-N-methyl-, O-n-propyl-N-ethyl-, O-n-propyl-N-n-propyl-, O-n-propyl-N-iso-propyl-, O-n-propyl-N-n-butyl-, O-n-propyl-N-sec.-butyl-, O-n-propyl-N-tert.-butyl-, O-iso-propyl-N-methyl-, O-iso-propyl-N-ethyl-, O-iso-propyl-N-n-propyl-, O-iso-propyl-N-iso-propyl-, O-iso-propyl-N-n-butyl-, O-iso-propyl-N-sec.-butyl-, O-iso-propyl-N-tert.-butyl-, O-n-butyl-N-methyl-, O-n-butyl-N-ethyl-, O-n-butyl-N-n-propyl-, O-n-butyl-N-iso-propyl-, O-tert.-butyl-N-ethyl-, O-tert.-butyl-N-n-propyl- or O-tert.-butyl-N-n-butyl-phosphoric acid ester-amide chloride, and also dimethane-, diethane-, di-n-propane-, di-iso-propane-, di-n-butane-, di-sec.-butane- or di-tert.-butane-phosphinic acid chloride and, in each case, the corresponding thiono analogues.

The 1-alkyl- and 1-phenyl-3-hydroxy-5-alkylmercapto-alkylmercapto-triazoles of the formula (III), some of which are new, can be prepared according to processes which are known in principle. For example, the following three processes can be used.

a. A halocarbonic acid alkyl ester is reacted with potassium thiocyanate and subsequently with an alkyl-hydrazone or phenylhydrazone to give the intermediate product of the formula

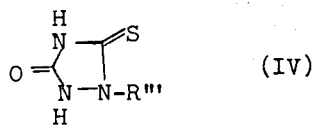

(IV)

in which

R''' has the abovementioned meaning, and this product can then be converted, by reaction with a halothioether in the presence of an alcoholate, into the desired hyroxytriazole of the formula (III).

b. A thiosemicarbazide derivative of the formula

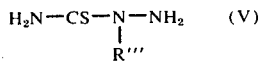

is reacted, for example with pyrocarbonic acid diethyl ester, to give an intermediate product of the formula

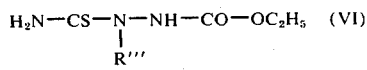

in which

R''' has the abovementioned meaning, and the compound (VI) is then cyclized with an alcoholate as indicated under (a) and subsequently reacted with a halothioether.

c. If R''' is alkyl, a carbonic acid alkyl ester hydrazide is reacted with an aldehyde or ketone to give an intermediate product of the formula

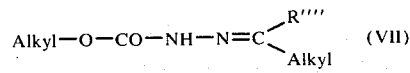

wherein

R'''' is hydrogen or alkyl, and the compound (VII) is reduced catalytically and reacted with thiocyanic acid, cyclized as indicated under (a) in the presence of an alcoholate and reacted with a halothioether.

The following may be mentioned individually as examples of triazole derivatives (III): 5-methylmercaptomethylmercapto-, 5-methylmercaptoethylmercapto-, 5-ethylmercaptomethylmercapto-, 5-ethylmercaptoethylmercapto- and 5-n-propylmercaptoethylmercapto-3-hydroxy-1-phenyl- and -1-methyl- and -1-ethyl-triazole-(1,2,4).

The reaction according to the invention for the preparation of the new compounds (I) is preferably carried out in the presence of a solvent which term includes a mere diluent. Practically all inert organic solvents can be used for this purpose. These include, in particular, aliphatic and aromatic optionally chlorinated hydrocarbons, for example benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, for example acetonitrile and propionitrile.

All customary acid-binding agents can be used as acid acceptors. Alkali metal carbonates and alkali metal alcoholates, such as sodium carbonate and potassium carbonate, sodium methylene and ethylate and potassium methylate and ethylate, have proved particularly suitable, as have aliphatic, aromatic and heterocyclic amines, for example triethylamine and trimethylamine, dimethylaniline, dimethylbenzylamine and pyridine.

The reaction temperature cam be varied within a wide range. In general, the reaction is carried out at 0° to 120°, preferably at 15° to 80° C.

The reaction is in general carried out under normal pressure.

In carrying out the process, the starting materials are in general employed in equimolar amounts. An excess of one or other reactant produces no significant advantages. The reaction is preferably carried out in one of the abovementioned solvents in the presence of an acid acceptor, at the stated temperature, while stirring the mixture, and after a reaction time of one to several hours, in most cases at elevated temperature, the batch may be worked up in the generally customary manner. In general, the reaction mixture is poured into water and taken up in an organic solvent, for example methylene chloride, the organic phase is washed and dried and the solvent is distilled off under reduced pressure.

Most of the new compounds are obtained in the form of oils, many of which can not be distilled without decomposition but can be freed from the last volatile constituents by so-called "slight distillation", that is to say prolonged heating under reduced pressure to moderately elevated temperatures, and can be purified in this way. They are characterized by the refractive index. Some of the new compounds are obtained in crystalline form with a sharp melting point.

As has already been mentioned, the O-triazolyl-(thiono)phosphoric(phosphonic, phosphinic) acid esters and esteramides according to the invention are distinguished by an excellent insecticidal, including soil-insecticidal, acaricidal and nematocidal activity. They are active against plant pests, hygiene pests and pests of stored products and couple a low phytotoxicity with a good action against both sucking and biting insects and mites.

For this reason, the compounds according to the invention can be employed successfully as pesticides in plant protection and in the hygiene field and the field of protection of stored products.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the current gall aphid (*Cryptomyzus korschelti*), the rosy apple aphid (*Sappaphis mali*), the mealy plum aphid (*Hyalopterus arundinis*) and the cherry blackfly (*Myzus cerasi*); in addition, scales and mealybugs (Coccina), for examples the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly and moth caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (Coleoptera), for example the granary weevil (*Sitophilus granarius* – *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes* spec.) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*), and bluebottle fly (*Calliphora erythrocephala*) as well as the stable fly (*Stomoxys calcitrans*); further, gnats, for example mosquitoes, such as the yellow fever mosquito (*Aedes aegypti*), the northern house mosquito (*Culex pipiens*) and the malaria mosquito (*Anopheles stephensi*).

With the mites (Acari) there are classed, in particular, the spider mites (Tetranychidae) such as the two-spotted spider mite (*Tetranychus urticae*) and the European red mite (*Paratetranychus pilosus* = *Panonychus ulmi*), gall mites, for example the blackcurrant gall mite (*Eriophyes ribis*), and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against hygiene pests and pests of stored products, particularly flies and mosquitoes, the process products are also distinguished by an outstanding residual activity on wood and clay, as well as a good stability to alkali on limed substrates.

The active compounds according to the invention couple a low toxicity to warm-blooded animals with powerful nematocidal properties and can therefore be used to combat nematodes, especially phytopathogenic nematodes. These essentially include leaf nematodes (Arphelenchoides), such as the chrysanthemum eelworm (*A. ritzemabosi*) the leaf-blotch eelworm (*A. fragariae*) and the rice eelworm (*A. oryzae*); stem nematodes (Ditylenchus), such as the stem eelworm (*D. Dipsaci*); rootknot nematodes (Meloidogyne), such as *M. arenaria* and *M. incognita*; cyst-forming nematodes (Heterodera), such as the potato cyst eelworm (*H. rostochiensis*) and the beet cyst eelworm (*H. schachtii*); and also free-living root nematodes, for example of the genera Pratylenchus, Paratylenchus, Rotylenchus, Xiphinema and Radopholus.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides, and nematocides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. insects, acarids and nematodes, which comprises applying to at least one of correspondingly (a) such insects, (b) such acarids, (c) such nematodes, and (d) the corresponding habitat thereof, i.e. the locus to be protected, e.g. to a growing crop to an area where a crop is to be grown or to a domestic animal, a correspondingly combative or toxic amount, i.e. an insecticidally, acaricidally or nematocidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Phaedon larvae test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After the specified periods of time, the degree of destruction was determined in %: 100% means that all beetle larvae had been killed whereas 0% means that none of the beetle larvae had been killed.

The active compounds, the concentrations of the active compounds, the evaluation times and the results can be seen from the following Table 1.

Table 1

(*Phaedon* larvae test)

| Active compound | Active compound concentration in % by weight | Degree of destruction in % after 3 days |
|---|---|---|
| (known) (B): $(CH_3O)_2P(S)-O-$[pyrazole with CH$_3$, NH-N] | 0.1 | 0 |
| (known) (A): $(C_2H_5O)_2P(S)-O-$[pyrazole with CH$_3$, NH-N] | 0.1<br>0.01<br>0.001 | 100<br>100<br>0 |
| (known) (C): $(CH_3O)_2P(S)-O-$[ring with SCH$_3$, N=, N-N-CH$_3$] | 0.1<br>0.01<br>0.001 | 100<br>100<br>0 |
| (known) (D): $(C_2H_5O)_2P(S)-O-$[ring with SCH$_3$, N=, N-N-CH$_3$] | 0.1<br>0.01<br>0.001 | 100<br>100<br>0 |
| (known) (E): $(CH_3O)_2P(S)-O-$[ring with SCH$_3$, N=, N-N-C$_2$H$_5$] | 0.1<br>0.01<br>0.001 | 100<br>100<br>0 |
| (14): $(C_2H_5O)_2P(S)-O-$[ring with SCH$_2$-SC$_2$H$_5$, N=, N-N-phenyl] | 0.1<br>0.01<br>0.001 | 100<br>100<br>85 |
| (16): $(C_2H_5O)(C_2H_5)P(S)-O-$[ring with SCH$_2$-SC$_2$H$_5$, N=, N-N-phenyl] | 0.1<br>0.01<br>0.001 | 100<br>100<br>85 |
| (2): $(C_2H_5O)_2P(S)-O-$[ring with SCH$_2$-SC$_2$H$_5$, N=, N-N-CH$_3$] | 0.1<br>0.01<br>0.001 | 100<br>100<br>95 |
| (4): $(CH_3O)_2P(S)-O-$[ring with SCH$_2$-SC$_2$H$_5$, N=, N-N-C$_3$H$_7$-iso] | 0.1<br>0.01<br>0.001 | 100<br>100<br>100 |

Table 1-continued (*Phaedon* larvae test)

| Active compound | Active compound concentration in % by weight | Degree of destruction in % after 3 days |
|---|---|---|
| Compound (3): diethoxy-P(=S)-O-C(=N-N(C3H7-iso))-C(CH3)=N- with SCH2-SC2H5 substituent | 0.1<br>0.01<br>0.001 | 100<br>100<br>100 |
| Compound (11): C2H5O, C2H5-P(=S)-O-C(=N-N(C3H7-iso))-C(CH3)=N- with SCH2-CH2-SC2H5 substituent | 0.1<br>0.01<br>0.001 | 100<br>100<br>90 |

EXAMPLE 2

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following Table 2:

Table 2

(*Myzus* test)

| Active compound | Active compound concentration in % by weight | Degree of destruction in % after 1 day |
|---|---|---|
| (known) (B): $(CH_3O)_2P(=S)-O-$ pyrazole with CH3, N-N-H | 0.1 | 0 |
| (14): $C_2H_5O$, $C_2H_5O$-P(=S)-O- triazole with SCH2-SC2H5, N-N-phenyl | 0.1 | 100 |
| (16): $C_2H_5O$, $C_2H_5$-P(=S)-O- triazole with SCH2-SC2H5, N-N-phenyl | 0.1 | 100 |

Table 2-continued (*Myzus* test)

| Active compound | Active compound concentration in % by weight | Degree of destruction in % after 1 day |
|---|---|---|
| (15) structure with $C_2H_5O$, P=O, $SCH_2-SC_2H_5$, N-N-phenyl | 0.1 | 100 |
| (18) structure with $C_2H_5O$, P=O, $SCH_2-CH_2-SC_2H_5$, N-N-phenyl | 0.1 | 100 |
| (2) structure with $C_2H_5O$, P=S, $SCH_2-SC_2H_5$, N-N-$CH_3$ | 0.1 | 100 |
| (4) structure with $CH_3O$, P=S, $SCH_2-SC_2H_5$, N-N-$C_3H_7$-iso | 0.1 | 100 |
| (3) structure with $C_2H_5O$, P=S, $SCH_2-SC_2H_5$, N-N-$C_3H_7$-iso | 0.1 | 100 |
| (5) structure with $C_2H_5O$, P=O, $SCH_2-SC_2H_5$, N-N-$C_3H_7$-iso | 0.1 | 100 |
| (9) structure with $CH_3O$, P=S, $SCH_2-CH_2-SC_2H_5$, N-N-$C_3H_7$-iso | 0.1 | 100 |
| (8) structure with $C_2H_5O$, P=S, $SCH_2-CH_2-SC_2H_5$, N-N-$C_3H_7$-iso | 0.1 | 100 |

Table 2-continued (*Myzus* test)

| Active compound | Active compound concentration in % by weight | Degree of destruction in % after 1 day |
|---|---|---|
| (11) $C_2H_5O$–P(=S)(–OC_2H_5)–O–C(=N–N(C_3H_7-iso))–SCH_2–CH_2–SC_2H_5 (with N in ring) | 0.1 | 100 |
| (10) $C_2H_5O$–P(=O)(–C_2H_5)–O–C(=N–N(C_3H_7-iso))–SCH_2–CH_2–SC_2H_5 | 0.1 | 100 |
| (12) iso-$C_3H_7NH$–P(=S)(–OC_2H_5O)–O–C(=N–N(C_3H_7-iso))–SCH_2–CH_2–SC_2H_5 | 0.1 | 100 |
| (20) $CH_3O$–P(=S)(–OCH_3)–O–C(=N–N(CH_3))–SCH_2–CH_2–SC_2H_5 | 0.1 | 100 |
| (19) $C_2H_5O$–P(=S)(–OC_2H_5)–O–C(=N–N(CH_3))–SCH_2–CH_2–SC_2H_5 | 0.1 | 100 |

EXAMPLE 3

Tetranychus test (resistant)
Solvent: 3 parts by weight of acetone
Emulsifer: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the common or two-spotted spider mite (*Tetranychus urticae*) in all stages of development.

After the specified periods of time, the effectiveness of the preparation of active compound was determined by counting the dead mites. The degree of destruction thus obtained was expressed as a percentage: 100% means that all the spider mites were killed whereas 0% means that none of the spider mites were killed.

The active compounds, the concentrations of the active compounds, the evaluation times and the results can be seen from the following Table 3:

Table 3

(*Tetranychus* test)

| Active compound | Active compound concentration in % by weight | Degree of destruction in % after 2 days |
|---|---|---|
|  (known) (B) | 0.1 | 0 |

Table 3-continued
(*Tetranychus* test)

| Active compound | Active compound concentration in % by weight | Degree of destruction in % after 2 days |
|---|---|---|
| (16) $C_2H_5O$, $C_2H_5$ – P(=S) – O – C(=N–N–C_6H_5)(–SCH_2–SC_2H_5) triazole with phenyl | 0.1 | 99 |
| (2) $(C_2H_5O)_2P(=S)–O–C(=N–N–CH_3)(–SCH_2–SC_2H_5)$ | 0.1 | 100 |
| (4) $(CH_3O)_2P(=S)–O–C(=N–N–C_3H_7\text{-iso})(–SCH_2–SC_2H_5)$ | 0.1 | 100 |
| (3) $(C_2H_5O)_2P(=S)–O–C(=N–N–C_3H_7\text{-iso})(–SCH_2–SC_2H_5)$ | 0.1 | 100 |
| (5) $(C_2H_5O)_2P(=O)–O–C(=N–N–C_3H_7\text{-iso})(–SCH_2–SC_2H_5)$ | 0.1 | 100 |
| (9) $(CH_3O)_2P(=S)–O–C(=N–N–C_3H_7\text{-iso})(–SCH_2–CH_2–SC_2H_5)$ | 0.1 | 90 |
| (8) $(C_2H_5O)_2P(=S)–O–C(=N–N–C_3H_7\text{-iso})(–SCH_2–CH_2–SC_2H_5)$ | 0.1 | 99 |
| (11) $C_2H_5O$, $C_2H_5$ – P(=S) – O – C(=N–N–C_3H_7\text{-iso})(–SCH_2–CH_2–SC_2H_5) | 0.1 | 100 |

Table 3-continued (*Tetranychus* test)

| Active compound | Active compound concentration in % by weight | Degree of destruction in % after 2 days |
|---|---|---|
| (EtO)$_2$P(O)-O-C(=N-N(C$_3$H$_7$-iso))-C(SCH$_2$CH$_2$SC$_2$H$_5$)=N (10) | 0.1 | 95 |
| (MeO)$_2$P(S)-O-C(=N-N-CH$_3$)-C(SCH$_2$CH$_2$SC$_2$H$_5$)=N (20) | 0.1 | 100 |
| (EtO)$_2$P(S)-O-C(=N-N-CH$_3$)-C(SCH$_2$CH$_2$SC$_2$H$_5$)=N (19) | 0.1 | 100 |

EXAMPLE 4

Critical concentration test/soil insects
Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration. The preparation of active compound was intimately mixed with the soil. The concentration of the active compound in the preparation was practically immaterial, the only decisive factor being the amount by weight of active compound per unit volume of soil, which is quoted in ppm (mg/l). The soil was filled into pots and the pots were left to stand at room temperature. After 24 hours the test insects were introduced into the treated soil and after a further 48 hours the degree of effectiveness of the active compound was determined in % by counting the dead and live test insects. The degree of effectiveness is 100% if all test insects were killed and is 0% if exactly as many test insects were still alive as in the case of the control.

The active compounds, amounts used and results can be seen from Table 4 which follows:

Table 4

(*Phorbia antiqua* grubs in the soil)

| Active compound | Active compound concentration in ppm | Degree of destruction in % |
|---|---|---|
| (CH$_3$O)$_2$P(S)-O-C(=N-N(CH$_3$))-C(S-CH$_3$)=N (C) | 20 | 0 |
| (C$_2$H$_5$O)$_2$P(S)-O-C(=N-N(C$_6$H$_5$))-C(SCH$_2$-SC$_2$H$_5$)=N (14) | 20<br>10<br>5 | 100<br>100<br>90 |

Table 4-continued

| (Phorbia antiqua grubs in the soil) Active compound | Active compound concentration in ppm | Degree of destruction in % |
|---|---|---|
| (16) C₂H₅O\P(S)(C₂H₅)—O—C(=N—N—C₆H₅)—C(SCH₂—SC₂H₅)=N | 20<br>10<br>5 | 100<br>100<br>90 |
| (11) C₂H₅O\P(S)(C₂H₅)—O—C(=N—N—C₃H₇-iso)—C(SCH₂—CH₂—SC₂H₅)=N | 20<br>10<br>5 | 100<br>100<br>100 |
| (6) C₆H₅\P(S)(C₂H₅O)—O—C(=N—N—C₃H₇-iso)—C(SCH₂—SC₂H₅)=N | 20<br>10 | 100<br>95 |
| (4) CH₃O\P(S)(CH₃O)—O—C(=N—N—C₃H₇-iso)—C(SCH₂—SC₂H₅)=N | 20<br>10 | 100<br>90 |

EXAMPLE 5

Critical concentration test/soil insects
Test insect: Meloidogyne incognita
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted in ppm (mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness is 100% if all test insects were killed and is 0% if exactly as many test insects were still alive as in the case of the untreated control.

The active compounds, amounts used and results can be seen from Table 5 which follows:

Table 5

| Active compound | Nematocide test (Meloidogyne incognita) Active compound concentration in ppm | Degree of destruction in % |
|---|---|---|
| (known) (G) C₆H₅\P(S)(C₂H₅O)—O—C(=N—N—C₃H₇i)—C(S—CH₃)=N | 20<br>10 | 0<br>0 |

Table 5-continued

Nematocide test (*Meloidogyne incognita*)

| Active compound | Active compound concentration in ppm 20 | Degree of destruction in % 10 |
|---|---|---|
| (F) (known) — dimethoxy P=S O–C(SCH₃)=N–N(C₃H₇i) structure | 0 | 0 |
| (H) (known) — HO–C=N–N(C₂H₅)–C(SCH₂CH=CH₂)= triazole | 0 | 0 |
| (8) (C₂H₅O)₂P(=S)–O–C(SCH₂CH₂SC₂H₅)=N–N–C₃H₇-iso | 100 | 100 |
| (11) (C₂H₅O)(C₂H₅)P(=S)–O–C(SCH₂CH₂SC₂H₅)=N–N–C₃H₇-iso | 100 | 100 |
| (2) (C₂H₅O)₂P(=S)–O–C(SCH₂SC₂H₅)=N–N–CH₃ | 100 | 100 |
| (3) (C₂H₅O)₂P(=S)–O–C(SCH₂SC₂H₅)=N–N–C₃H₇-iso | 100 | 100 |
| (12) iso-C₃H₇NH(C₂H₅O)P(=S)–O–C(SCH₂CH₂SC₂H₅)=N–N–C₃H₇-iso | 100 | 100 |

The preparation of the novel compounds is illustrated in the following examples:

EXAMPLE 6

(a)
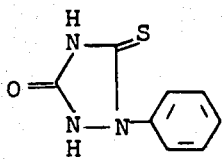

109 g of chlorocarbonic acid ethyl ester were added to 96 g (1 mole) of dried potassium thiocyanate suspended in 500 ml of dry acetone at 30° to 40° C. The mixture was stirred overnight. A solution which had been prepared by dropwise addition of 108 g of phenylhydrazine to 200 ml of acetone at 40° to 45° C, stirring for a further three hours, pouring into benzene, drying and evaporating the solvent was then added. The reaction mixture was stirred overnight, filtered and evaporated and the residue was boiled with 800 ml of water and 100 ml of hydrochloric acid under reflux at 30° C. After cooling, the precipitate was filtered off and recrystallized from acetonitrile; 48 g (25% of theory) of 1-phenyl-3-oxo-5-thiono-triazolidine-(1,2,4) of melting point 235° C were obtained.

The compound of the following formula

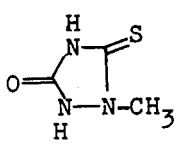

was prepared analogously, in 65% yield, and with melting point 250° C.

($a_1$)

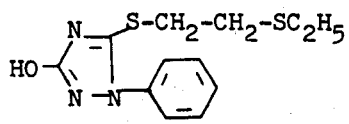

0.5 mole of a sodium methylate solution and 63 g of β-chloroethyl-ethyl-thioether were added to a solution of 97 g (0.5 mole) of the product obtained as described under a), in 400 ml of ethanol, the reaction mixture was stirred for 4 hours at 70° C and cooled, the batch was poured into water and the precipitate was filtered off and recrystallized from acetonitrile. 94 g (67% of theory) of 1-phenyl-3-hydroxy-5-ethylmercaptoethyl-mercaptotriazole-(1,2,4) of melting point 110° C were obtained.

The compounds of the following formulae were prepared analogously:

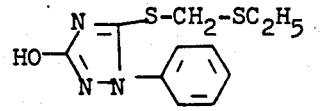

in 69% yield, with melting point 119° C, and

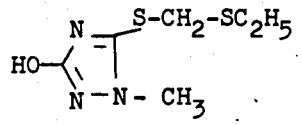

in 28% yield, with melting point 73° C.

(b)

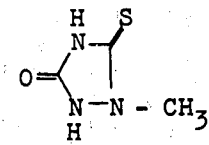

A mixture of 35.4 g (0.2 mole of

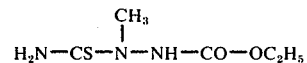

(prepared from methylthiosemicarbazide and pyrocarbonic acid diethyl ester), of melting point 170° C, and 0.2 mole of sodium methylate (dissolved in 100 ml of methanol) was heated for 5 hours under reflux and then evaporated under reduced pressure, and the residue was dissolved in water and reprecipitated with hydrochloric acid. 17 g (6% of theory) of 1-methyl-3-oxo-5-thio-triazolidine-(1,2,4) of melting point 250° C were obtained.

The further reaction with a halothioether was carried out as described under ($a_1$).

c. $C_2H_5O$-CO-NH-NH-$C_3H_7$-iso

A solution of carbonic acid ethyl ester hydrazone

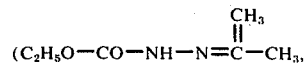

prepared from carbonic acid ethyl ester hydrazide and acetone), of melting point 70° C, in 500 ml of ethanol, was hydrogenated with 10 g of a 5% strength platinum-on-charcoal catalyst under high pressure at 60° C, the reaction mixture was then filtered, the solvent was evaporated off and the residue was distilled at 87° C/6 mm Hg. 110 g (76% of theory) of N-iso-propylcarbonic acid ethyl ester hydrazide of refractive index $n_D^{20}$: 1.4362 were obtained.

($c_1$)

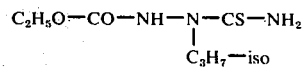

45 ml of concentrated hydrochloric acid followed by 50 g of potassium thiocyanate were added to a solution of 73 g (0.5 mole) of the product obtained as described under (c), in 200 ml of water, the reaction mixture was briefly boiled up and evaporated under a pressure of 30 mm Hg, and the residue was then heated to 100° C for 2 hours. The batch was then cooled and recrystallized from water. The product of the above formula was obtained in 68% yield, and with melting point 168° C.

($c_2$)

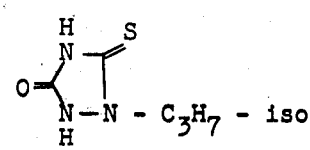

1 mole of sodium methylate solution was added to a solution of 205 g (1 mole) of the product obtained as described under ($c_1$), in 400 ml of methanol, and the batch was boiled for 8 hours under reflux. The reaction solution was then evaporated and the residue was suspended in a little water. The mixture was acidified with 80 ml of pure concentrated hydrochloric acid and the precipitate was filtered off, washed and recrystallized from methanol. 96 g (60% of theory) of 1-iso-propyl-3-oxo-5-thio-triazolidine-(1,2,4) of melting point 228° C were obtained.

($c_3$)

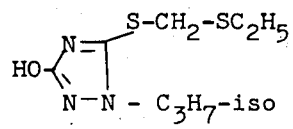

1 mole of sodium methylate solution was added to a solution of 159 g (1 mole) of the product obtained as described under ($c_2$), in 700 ml of methanol, and 115 g of chloromethylethyl-thioether were then added dropwise to the reaction mixture at 5° to 10° C. After stirring for 3 hours, the precipitate was filtered off and the solution was evaporated. The residue which remained was triturated with ligroin. 147 g (63% of theory) of 1-iso-propyl-3-hydroxy-5-ethylmercaptomethylmer-captotriazole-(1,2,4) of melting point 86° C were obtained.

The compound of the following formula

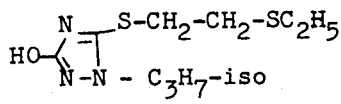

was prepared, analogously to the description under ($c_1$) – ($c_3$), in 59% yield and with melting point 60° C.

(d)

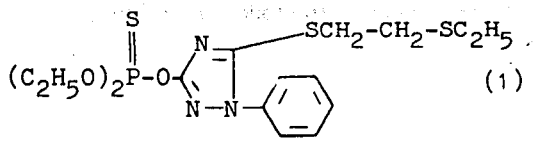

19 g (0.1 mole) of 0,0-diethylthionophosphoric acid diester chloride were added to a mixture of 28 g (0.1 mole) of 1-phenyl-3-hydroxy-5-ethylmercaptoethyl-mercaptotriazole(1,2,4) in 200 ml of acetonitrile and 15 g of potassium carbonate, and after stirring for 4 hours at 80° C the reaction solution was poured into water and taken up in methylene chloride. The organic phase was washed and dried. The solvent was then distilled off under reduced pressure. The residue was subjected to "slight distillation". This gave 33 g (76% of theory) of 0,0-diethyl-0-[1-phenyl-5-ethylmercapto-ethylmercapto-1,2,4-triazol(3)yl]-thionophosphoric acid ester of refractive index $n_D^{22} = 1.5702$.

The compounds of the formula

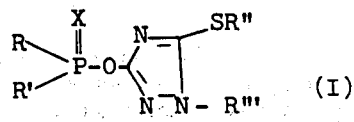

identified below were prepared analogously

| Compound No. | R | R' | X | R'' | R''' | Refractive index |
|---|---|---|---|---|---|---|
| 2 | —OC$_2$H$_5$ | —OC$_2$H$_5$ | S | —CH$_2$—SC$_2$H$_5$ | —CH$_3$ | $n_D^{22}$ : 1,5379 |
| 3 | —OC$_2$H$_5$ | —OC$_2$H$_5$ | S | —CH$_2$—SC$_2$H$_5$ | —C$_3$H$_7$—iso | $n_D^{22}$ : 1,5232 |
| 4 | —OCH$_3$ | —OCH$_3$ | S | —CH$_2$—SC$_2$H$_5$ | —C$_3$H$_7$—iso | $n_D^{22}$ : 1,5377 |
| 5 | —OC$_2$H$_5$ | —OC$_2$H$_5$ | O | —CH$_2$—SC$_2$H$_5$ | —C$_3$H$_7$—iso | $n_D^{22}$ : 1,5065 |
| 6 | —OC$_2$H$_5$ | —⟨phenyl⟩ | S | —CH$_2$—SC$_2$H$_5$ | —C$_3$H$_7$—iso | $n_D^{22}$ : 1,5738 |
| 7 | —CH$_3$ | —CH$_3$ | S | —CH$_2$—SC$_2$H$_5$ | —C$_3$H$_7$—iso | $n_D^{22}$ : 1,5630 |
| 8 | —OC$_2$H$_5$ | —OC$_2$H$_5$ | S | —CH$_2$—CH$_2$—SC$_2$H$_5$ | —C$_3$H$_7$—iso | $n_D^{23}$ : 1,5231 |
| 9 | —OCH$_3$ | —OCH$_3$ | S | —CH$_2$—CH$_2$—SC$_2$H$_5$ | —C$_3$H$_7$—iso | $n_D^{22}$ : 1,5351 |
| 10 | —OC$_2$H$_5$ | —OC$_2$H$_5$ | O | —CH$_2$—CH$_2$—SC$_2$H$_5$ | —C$_3$H$_7$—iso | $n_D^{22}$ : 1,5049 |
| 11 | —C$_2$H$_5$ | —OC$_2$H$_5$ | S | —CH$_2$—CH$_2$—SC$_2$H$_5$ | —C$_3$H$_7$—iso | $n_D^{22}$ : 1,5350 |
| 12 | —OC$_2$H$_5$ | —NH—C$_3$H$_7$—iso | S | —CH$_2$—CH$_2$—SC$_2$H$_5$ | —C$_3$H$_7$—iso | $n_D^{22}$ : 1,5320 |
| 13 | —CH$_3$ | —CH$_3$ | S | —CH$_2$—CH$_2$—SC$_2$H$_5$ | —C$_3$H$_7$—iso | $n_D^{22}$ : 1,5580 |
| 14 | —OC$_2$H$_5$ | —OC$_2$H$_5$ | S | —CH$_2$—SC$_2$H$_5$ | —⟨phenyl⟩ | $n_D^{22}$ : 1,5738 |
| 15 | —OC$_2$H$_5$ | —OC$_2$H$_5$ | O | —CH$_2$—SC$_2$H$_5$ | —⟨phenyl⟩ | $n_D^{22}$ : 1,5528 |
| 16 | —C$_2$H$_5$ | —OC$_2$H$_5$ | S | —CH$_2$—SC$_2$H$_5$ | —⟨phenyl⟩ | $n_D^{22}$ : 1,5890 |

-continued

| Compound No. | R | R' | X | R'' | R''' | Refractive index |
|---|---|---|---|---|---|---|
| 17 | —OCH₃ | —OCH₃ | S | —CH₂—CH₂—SC₂H₅ |  | $n_D^{22}$ : 1,5852 |
| 18 | —OC₂H₅ | —OC₂H₅ | O | —CH₂—CH₂—SC₂H₅ |  | $n_D^{22}$ : 1,5532 |
| 19 | —OC₂H₅ | —OC₂H₅ | S | —CH₂—CH₂—SC₂H₅ | —CH₃ | $n_D^{23}$ : 1,5350 |
| 20 | —OCH₃ | —OCH₃ | S | —CH₂—CH₂—SC₂H₅ | —CH₃ | $n_D^{23}$ : 1,5513 |

Other compounds which can be similarly prepared include:

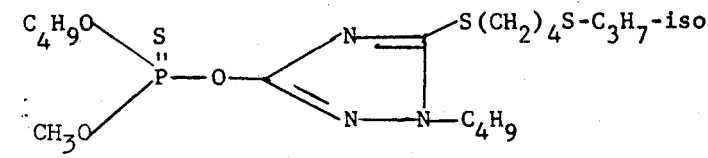

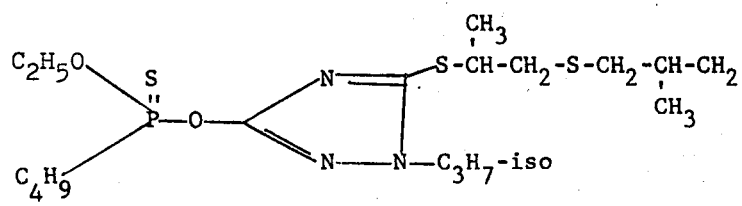

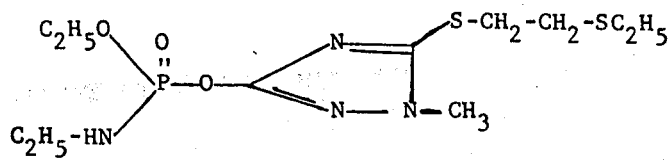

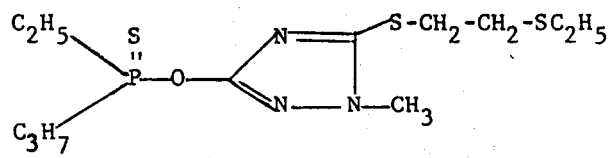

and the like.

It will be appreciated that the instant specification and Examples are set forth by way of illustration and not limitation and that various modifications and changes may be made without departing from the spirit and scope of the present invention.

What is claimed is:
1. An O-[1-alkyl or-phenyl-5-alkylmercaptoalkylmercapto 1,2,4-triazol(3)yl-(thiono)-phosphoric(phosphonic, phosphinic) acid ester or ester-amide of the formula

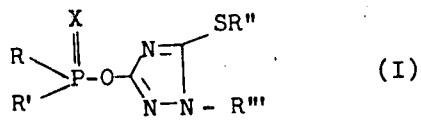

(I)

in which
R is alkyl or alkoxy, each with 1 to 6 carbon atoms,
R' is alkyl, alkoxy or alkylamino, each with 1 to 6 carbon atoms, or phenyl,
R'' is alkylmercaptoalkyl with 1 to 4 carbon atoms in each alkyl moiety,
R''' is alkyl with 1 to 4 carbon atoms or phenyl, and
X is oxygen or sulfur.

2. A compound according to claim 1 in which R is alkyl or alkoxy with 1 to 4 carbon atoms, R' is alkyl, alkoxy or alkylamino with 1 to 5 carbon atoms, or phenyl, R'' is alkylmercaptoalkyl with 1 to 3 carbon atoms in each alkyl moiety, and R''' is alkyl with 1 to 3 carbon atoms, or phenyl.

3. A compound according to claim 1 wherein such compound is 0,0-diethyl-0-[1-isopropyl-5-ethylmercaptomethylmercapto1,2,4-triazol(3)yl]-thionophosphoric acid ester of the formula

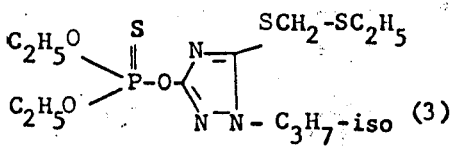 (3)

4. A compound according to claim 1 wherein such compound is 0,0-diethyl-0-[1-isopropyl-5-ethylmercaptoethylmercapto1,2,4-triazol(3)yl]-thionophosphoric acid ester of the formula

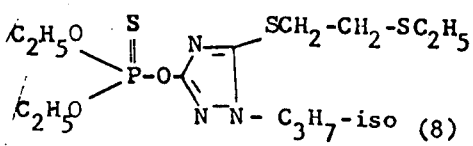 (8)

5. A compound according to claim 1 wherein such compound is 0-ethyl-0[1-isopropyl-5-ethylmercaptoethylmercapto1,2,4-triazol(3)yl]-ethanethionophosphonic acid ester of the formula

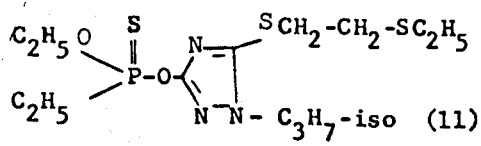 (11)

6. A compound according to claim 1 wherein such compound is 0-ethyl-0[1-phenyl-5-ethylmercaptomethylmercapto-1,2,4-triazol(3)yl]-ethanethionophosphonic acid ester of the formula

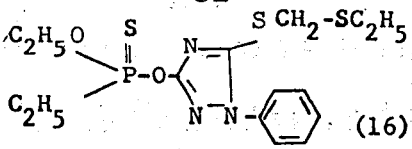 (16)

7. A compound according to claim 1 wherein such compound is 0,0-diethyl-0-[1-methyl-5-ethylmercaptoethylmercapto-1,2,4-triazol(3)yl]-thionophosphoric acid ester of the formula

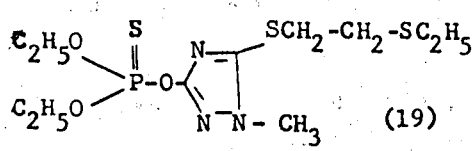 (19)

8. An insecticidal, acaricidal or nematocidal composition containing as active ingredients or insecticidally, acaricidally or nematocidally effective amount of a compound according to claim 1 in admixture with a diluent.

9. A method of combating insect, acarid or nematode pests which comprises applying to the pests or a habitat thereof an insecticidally, acaricidally or nematocidally effective amount of a compound according to claim 1.

10. The method according to claim 9 in which said compound is:

0,0-diethyl-0-[1-isopropyl-5-ethylmercaptomethylmercapto-1,2,4-triazol(3)yl]-thionophosphoric acid ester, 0,0-diethyl-0-[1-isopropyl-5-ethylmercaptoethylmercapto-1,2,4-triazol(3)yl]-thionophosphoric acid ester, 0-ethyl-0[1-isopropyl-5-ethylmercaptoethylmercapto-1,2,4-triazol(3)yl]-ethanethiophosphonic acid ester, 0-ethyl-0-[1-phenyl-5-ethylmercaptomethylmercapto-1,2,4-triazol(3)yl]-ethanethionophosphonic acid ester, or 0,0-diethyl-0-[1-methyl-5-ethylmercapto-ethylmercapto-1,2,4-triazol(3)yl]-thionophosphoric acid ester.

* * * * *

UNITED STATES PATENT AND TRADEMARK OFFICE
CERTIFICATE OF CORRECTION

PATENT NO. : 3,985,874
DATED : October 12, 1976
INVENTOR(S) : Hellmut Hoffmann et al It is certified that error appears in the above-identified patent and that said Letters Patent are hereby corrected as shown below:

Col. 2, line 60  cancel "ester-aimide" and substitute --ester-amide--

Col. 3, line 52  cancel "hyroxytriazole" and substitute --hydroxytriazole--

Col. 4, line 40  cancel "methylene" and substitute --methylate--

Col. 32, line 26  cancel "or" and substitute --an--

Signed and Sealed this ninth Day of August 1977

[SEAL]

Attest:

RUTH C. MASON
Attesting Officer

C. MARSHALL DANN
Commissioner of Patents and Trademarks